(12) United States Patent
Massen

(10) Patent No.: US 7,298,890 B2
(45) Date of Patent: Nov. 20, 2007

(54) METHOD AND ARRANGEMENT FOR THE PHOTOGRAPHICALLY DETECTING THE SPATIAL FORM OF AN OBJECT

(75) Inventor: Robert Massen, Ohningen-Wangen (DE)

(73) Assignee: corpus.e AG, Stuttgart (DE)

( * ) Notice: Subject to any disclaimer, the term of this patent is extended or adjusted under 35 U.S.C. 154(b) by 883 days.

(21) Appl. No.: 10/472,203

(22) PCT Filed: Mar. 14, 2002

(86) PCT No.: PCT/EP02/02875

§ 371 (c)(1),
(2), (4) Date: Sep. 22, 2003

(87) PCT Pub. No.: WO02/074038

PCT Pub. Date: Sep. 26, 2002

(65) Prior Publication Data
US 2004/0228517 A1 Nov. 18, 2004

(30) Foreign Application Priority Data
Mar. 18, 2001 (DE) .............................. 101 13 211

(51) Int. Cl.
G06K 9/00 (2006.01)
G06K 9/36 (2006.01)
G01C 9/00 (2006.01)
(52) U.S. Cl. .................. 382/154; 382/100; 382/291; 702/153
(58) Field of Classification Search ............. 382/103, 382/154, 291, 100; 345/420; 701/23; 396/429; 530/350; 180/168; 340/551; 360/32; 435/252.3, 435/320.1, 6, 69.1, 325; 401/41; 356/620; 283/93; 702/153
See application file for complete search history.

(56) References Cited

U.S. PATENT DOCUMENTS 4,745,290 A 5/1988 Frankel et al.

(Continued)

FOREIGN PATENT DOCUMENTS

AT 3 63 580 1/1981

(Continued)

Primary Examiner—Sheela Chawan
(74) Attorney, Agent, or Firm—Stuart J. Friedman

(57) ABSTRACT

A method of detecting the 3D shape of an object by photogrammetry, in which a plurality of photogrammetric point markers and a plurality of connecting markers are provided on the surface of the object, each connecting marker connecting a subset of the plurality of point markers with each other, with at least two different types of point markers existing that differ from each other in their optical configuration, and some of the point markers provided along a connecting marker are formed in such a way that the sequence of their optical configurations results in a predetermined code that characterizes the respective connecting marker, a plurality of photogrammetric images of the object are taken from different views, an image processing of the images is performed, in which first the connecting markers mutually corresponding to each other in the images are associated with one another using their respective code, and then the point markers connected with each other by the respective connecting marker are associated with one another with the aid of the connecting marker association in the images, and using the point marker association, the 3D shape of the object is determined by means of a photogrammetric evaluation process. The invention further relates to an arrangement for carrying out the method.

21 Claims, 5 Drawing Sheets

U.S. PATENT DOCUMENTS

| | | | |
|---|---|---|---|
| 4,825,263 A | 4/1989 | Desjardins et al. | |
| 5,127,420 A | 7/1992 | Horvath | |
| 5,911,126 A | 6/1999 | Massen | |
| 2003/0142863 A1* | 7/2003 | Massen | 382/154 |

FOREIGN PATENT DOCUMENTS

| | | |
|---|---|---|
| DE | 78 310 | 12/1970 |
| DE | 31 19 857 | 12/1982 |
| DE | 42 32 606 | 3/1994 |
| DE | 43 35 121 | 5/1995 |
| DE | 196 26 889 | 1/1998 |
| WO | WO 92/08175 | 5/1992 |
| WO | WO 95/31934 | 11/1995 |
| WO | WO 97/14932 | 4/1997 |

* cited by examiner

Image A5

Image A4

METHOD AND ARRANGEMENT FOR THE PHOTOGRAPHICALLY DETECTING THE SPATIAL FORM OF AN OBJECT

FIELD OF THE INVENTION

The invention relates to a method and an arrangement for the photogrammetric detection of the 3D shape of an object.

BACKGROUND OF THE INVENTION

In connection with the so-called "mass customization", i.e. the production and sale of products individually adapted to the body measurements of a customer, the detection of the three-dimensional spatial shape of the body or of body parts is an important problem to be solved in engineering. When the three-dimensional spatial shape of a body part e.g. the torso/leg region of a customer, is known, individual articles of clothing such as pants, shirts, etc. may be manufactured with a very good fit.

A number of body scanners have been developed which detect and digitize the three-dimensional shape of the human body or of body parts contactlessly, using various optical methods, e.g. laser triangulation, stereo methods, moirémethods, etc., in which the data records describing the digitization are then made available for the automated production of individually adapted products. As a rule, such body scanners operate with technically very sophisticated and expensive processes which, in addition, require optical calibration and can therefore be employed only by trained specialist staff.

The so-called passive methods of short-range photogrammetry are considerably more cost-effective since merely calibrated cameras or digital cameras are required, rather than expensive projection units or precisely calibrated mechanical structures.

For instance, the Patent EP 0 760 622, "Sensing Process and Arrangement for the Three-Dimensional Shape in Space of Bodies or Body Parts", the applicant and inventor of which is Robert Massen, discloses a method which allows an optical detection of the 3D coordinates of a body or body part, involving very little technical expenditure. To this end, the body is covered with an elastic envelope specially marked with precisely located point markers, and photographs of the body are taken from a plurality of camera positions that overlap but are otherwise taken free-handed. By a photogrammetric evaluation of the corresponding point markers in the individual overlapping image areas of the photographs, a 3D data record of the body part may be established.

In order to allow a 3D reconstruction of the body part from the point markers provided on the body part or on an envelope pulled over the body part based on two overlapping image recordings using methods of photogrammetry, the pixel coordinates of the so-called homologous point markers, i.e. of the point markers mutually corresponding to each other in the images need to be determined. This process is also referred to as registration. Therefore, in an automatic registration, those point markers which correspond to each other need to be found from two overlapping image recordings using methods of two-dimensional image processing. In previous known methods, this is achieved by the use of individually encoded point markers. The point markers used are circles, for example, that are surrounded by radial segments representing a binary code (in this connection see the left-hand part of FIG. 1). Here, the center of the encoded marker defines the location of the photogrammetric point marker. The radial segments provide a unique characterization for each point marker by a code of its own.

In the prior art methods, attempts are made with the aid of automatic image processing to find such point markers in two images, to read their code and to prepare a list of the corresponding point markers, i.e. the homologous point markers. Once preparation of this list is complete, the known methods of image orientation and bundle adjustment may be employed to establish a 3D data record containing the XYZ space coordinates of all homologous point markers.

In the photogrammetric measurement of large structures such as vessel hulls, aircraft parts etc., the space required by such encoded point markers is not relevant. However, a disadvantage of the prior art methods for the photogrammetric determination of the 3D shape of an object, which make use of individually encoded point markers that cover a relatively large area consists in that these methods are not suitable for the digitization of very small objects, which need to be covered with many point markers due to the required spatial point density. When using encoded point markers as are illustrated in FIG. 1, for example, in such cases the space offered by the surface of the object is not sufficient for achieving the spatial point density necessary for a good photogrammetric measurement.

In German Patent Application Serial Number 100 25 922.7 entitled "Automatische photogrammetrische Digitalisierung von Körpern und Objekten" ("Automatic Photogrammetric Digitization of Bodies and Objects"), the applicant and inventor of which is Robert Massen, it is in addition proposed to provide area markers on the envelope described in EP 0 760 622, which each comprise a plurality of point markers and form a background of the point markers, the surface area of the area markers having a particular color. The use of color image processing methods allows an easy automatic determination of the area markers (regions) corresponding in the different photogrammetric images and then of the corresponding point markers (so-called homologous pixels) therefrom. Once the list of the homologous pixels is available, the 3D data of the entire body part may be calculated using the methods of image orientation and bundle adjustment that are familiar to a person of ordinary skill in the art of photogrammetry.

A drawback of this method is that a relatively large number of different colors are needed for marking. Therefore, the color fidelity of the cameras employed must be sufficiently high and stable to be able to adequately differentiate between such multitude of different colors in an automatic recognition. Also, the standards applied to constancy and color fidelity of the illumination are higher than those in a marking technique, which would manage with only very few colors that are distinctly different in the color space. A further disadvantage of this method resides in the relatively high geometric resolution required for optically resolving the color edges and color corners used as markers.

Both requirements, high color fidelity and high geometric resolution, can not be satisfied by simple and very low-priced cameras such as for instance by webcams based on CMOS image sensors or image sensors incorporated in future mobile telephones and so-called personal organizers (pocket computers). Thus, it is not possible for such very simple and inexpensive image recording devices to be used for a simple digitization of body parts as described above.

Therefore, a technical and economic interest exists in providing a method and an arrangement for the photogrammetric detection of the 3D shape of an object, featuring an improved marking technique that allows a low-cost and simple measurement even of small objects.

Furthermore, there exists an interest in a method and an arrangement for the photogrammetric detection of the 3D shape of an object that—with regard to the marking—manage with only few different colors and only relatively rough structures, in order to enable an automatic determination of homologous pixels from a plurality of overlapping image recordings using inexpensive, low color fidelity and low resolution cameras and imaging devices and with an illumination that may be of low definition in respect of the color. This would permit to employ the method even when using low-priced webcams (web cameras) or digital cameras, for example, that are commonly used today and are rather poorly specified as regards color fidelity and resolution.

SUMMARY OF THE INVENTION

The interest as set forth above in this field of engineering is met in accordance with the invention by a method of detecting the 3D shape of an object by photogrammetry, in which a plurality of photogrammetric point markers and a plurality of connecting markers are provided on the surface of the object, each connecting marker connecting a subset of the plurality of point markers with each other, with at least two different types of point markers existing that differ from each other in their optical configuration, and some of the point markers provided along a connecting marker are formed in such a way that the sequence of their optical configurations results in a predetermined code that characterizes the respective connecting marker, a plurality of photogrammetric images of the object are taken from different views, an image processing of the images is performed, in which first the connecting markers mutually corresponding to each other in the images are associated with one another using their respective code, and then the point markers connected with each other by the respective connecting marker are associated with one another with the aid of the connecting marker association in the images, and using the point marker association, the 3D shape of the object is determined by means of a photogrammetric evaluation process.

The interest described above is further satisfied by an arrangement for detecting the 3D shape of an object by photogrammetry, which comprises an imaging system for obtaining photogrammetric images of different views of the object and a system for processing and evaluating the images and for determining the 3D shape of the object and is characterized in that the arrangement further includes a plurality of photogrammetric point markers and a plurality of connecting markers on the surface of the object, each connecting marker connecting a subset of the plurality of point markers with each other, with at least two different types of point markers existing that differ from each other in their optical configuration, and some of the point markers provided along a connecting marker being formed in such a way that the sequence of their optical configurations results in a predetermined code that characterizes the respective connecting marker.

Because of the fact that according to the invention it is not the point markers themselves that are encoded individually, but a characteristic sequence of point markers of different types results in a code, an easy automatic photogrammetric detection of even very small objects that require a high point marker density is made possible.

Advantageous further developments of the invention are characterized in the dependent claims.

BRIEF DESCRIPTION OF THE DRAWINGS

Further features and advantages of the invention will be apparent from the following description of an embodiment with reference to the drawings, in which.

DETAILED DESCRIPTION OF THE INVENTION

The invention will now be described by way of example, which is not to be construed in a limiting sense, with reference to the photogrammetric detection of the 3D shape of a knee region for the purpose of an automatic production of a knee orthesis.

Assuming, for example, that the knee is covered with an elastic envelope having photogrammetric markers applied thereto. The photogrammetric markers may however also be applied by a variety of other methods. For instance, the markers may be provided on the object by applying paint such as make-up directly onto the object, by projection with the aid of a projection system, or by sticking self-adhesive films onto the object which have the markers applied thereto.

Figure 2:
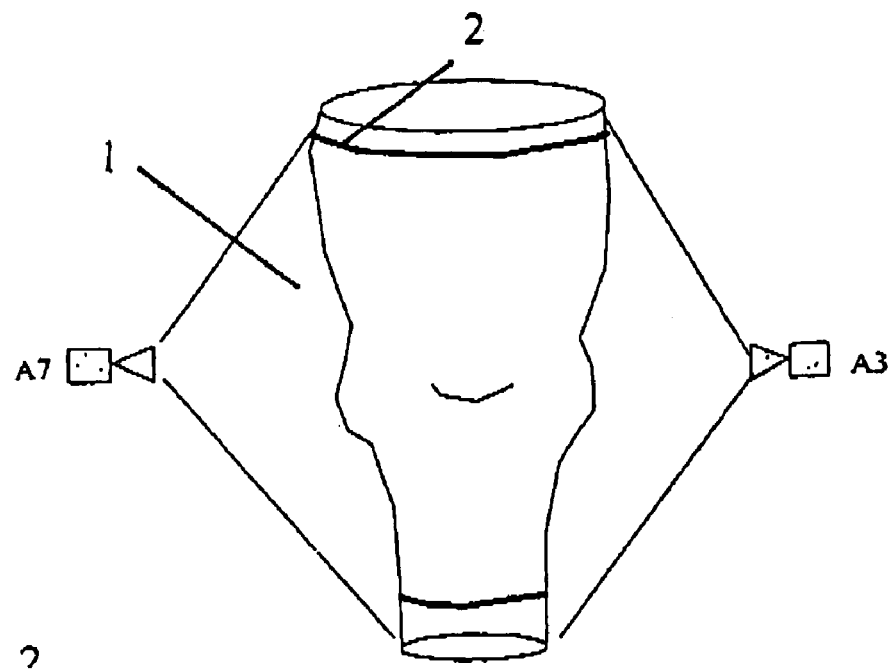
FIG. 2 is a side view of a knee to be digitized using the method according to the invention and provided with an envelope, and of a camera in two different imaging positions.

The knee 1 illustrated in FIG. 2, shown with the adjoining thigh and lower leg regions, which is to be digitized by way of example, roughly has a cylindrical basic shape. The required overlapping photographic images are expediently taken in this case in the form of views from all around the cylindrical body part; to ensure sufficient overlap, about 8 to 10 images distributed over the periphery are needed.

Figure 3:
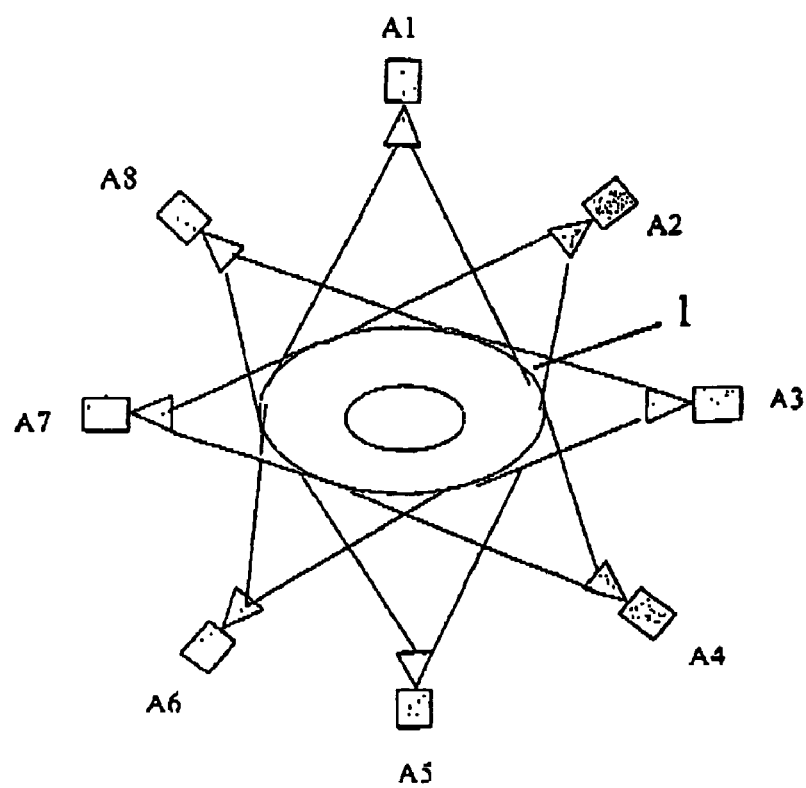
FIG. 3 is a top view of the knee illustrated in FIG. 2, with a representation of the imaging positions of a camera radially distributed about the knee.

FIG. 3 shows how a patient's knee region 1, clad in a marked elastic envelope (2 in FIG. 2), is imaged from eight radial positions, A1 to A8, using a camera. FIG. 2 shows a side view of the knee in which the camera can be seen only in the positions A3 and A7. For the photogrammetric evaluation it is merely important in this connection that the angular overlap area of the individual images includes a sufficient number of homologous, i.e. mutually corresponding, photogrammetric point markers. For obtaining such sequence of images from all around, the camera may for instance be manually guided around the leg at the same level.

Figure 4:
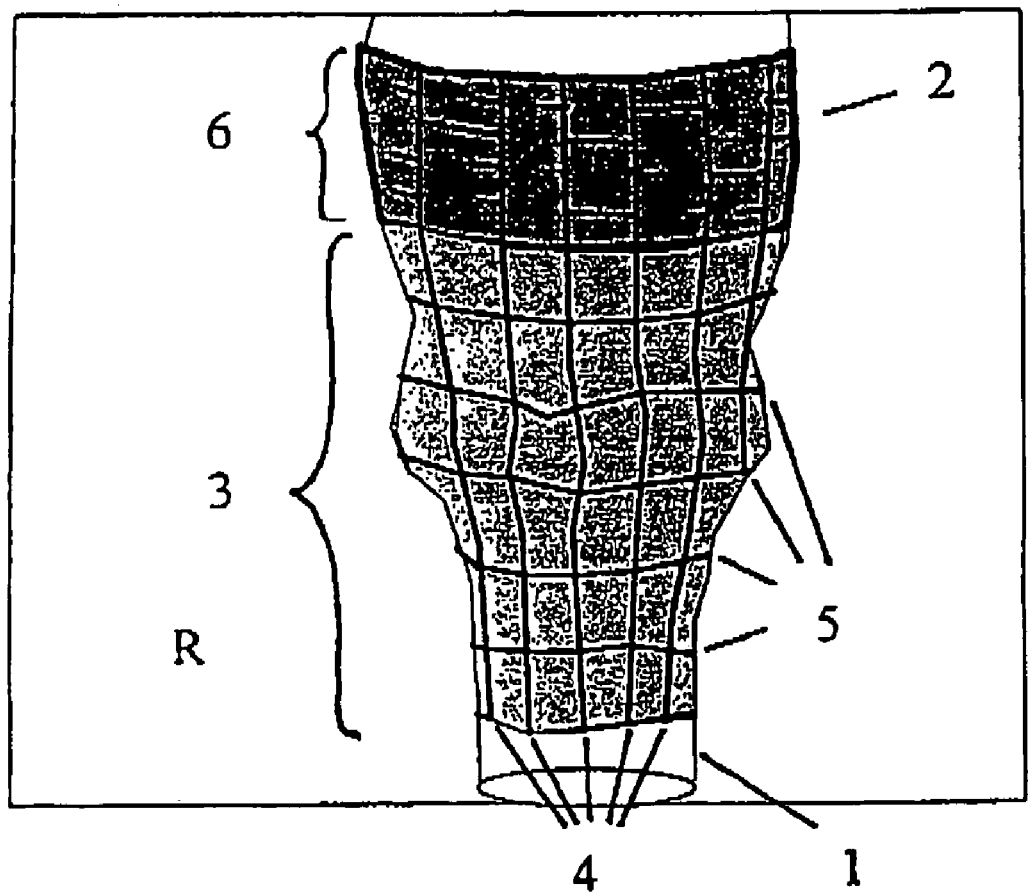
FIG. 4 shows a knee envelope photogrammetrically marked in accordance with a first embodiment of the invention.

FIG. 4 shows the knee region 1 with the elastic envelope 2, which has different photogrammetric markings according to the invention applied to it.

In its lower area 3 the envelope 2 is dyed in a first color that forms a distinct contrast to the spatial background R likewise acquired by the cameras and is represented by a light shade of gray in FIG. 4. The color selected will suitably be a color that is rather rare in everyday surroundings, such as pink. Grid lines are applied on the light shade of gray, the points of intersection of the vertical and horizontal grid lines 4 and 5 forming accurately located photogrammetric point markers which will hereinafter also be referred to as point markers not contributing to encoding because they can not be distinguished from one another and do not contain a code and are unable to serve for encoding.

In its upper area 6 the envelope 2 is dyed in a second color that forms a sharp contrast to the spatial background R and a sharp contrast to the first color of the lower area 3 (e.g., light green). The second color is represented by a dark shade of gray in FIG. 4. The vertical lines 4 of the grid structure of the lower area 3 also extend into the upper area.

In the upper area 6 the point markers are formed in that a relatively short horizontal line runs toward a vertical line 4 to end at the vertical line, the meeting point defining the precisely located point marker. As can be seen in FIG. 4, there are two different types of point markers here, namely those in which the relatively short horizontal line runs toward the vertical line of the grid structure from the left and those in which the relatively short horizontal line runs toward the vertical line of the grid structure from the right.

Along each vertical line 4 of the grid structure, in the following also referred to as connecting marker since it connects various point markers with one another, there are arranged in the upper colored area 6 four point markers whose sequence, i.e. the sequence of the arrangement of their horizontal lines (e.g., running toward the vertical line from the left, from the right, from the left, from the left), uniquely identifies the respective connecting marker. The connecting markers connect point markers located in the upper area 6 with the point markers located in the lower area 3.

With the aid of a simple color classification, carried out pixel by pixel, the "KNEE" region in each image recorded can already be automatically segmented from the background based on the first color, and the code region 6 within the "KNEE" region can be localized by the second color. A person of ordinary skill in the art of image processing knows how to robustly carry out such automatic color segmentations (cf., e.g., Robert Massen: "Form und Farbe: Farbbildverarbeitung für die industrielle Überwachung in Echtzeit" ("Shape and Color: Color Image Processing for Real-Time Industrial Monitoring"), in: Maschinelles Sehen, Europa-Fachpresse publishing house, 1990, ISBN 3-87207-004-5).

The markers required for photogrammetric evaluation point and connecting markers) are represented by black high-contrast lines, the size of the width of these lines being selected such that they can still be imaged even by inexpensive cameras usually featuring only low resolution. The points of intersection of the lines and, in the code area 6, the points of encounter, respectively, represent the actual photogrammetric point markers. The position of the point markers may be determined with high accuracy with the aid of interpolation methods (sub-pixel interpolation), so that in spite of a poor geometric camera resolution precisely located point marker coordinates may be measured. Using such sub-pixel interpolations known to a person of ordinary skill in the art of image processing, it is possible in this way to determine the XY position of the center of mass of a grid crossing with a precision which is about 5 to 10 times higher man the size of the imaging pixel.

The connecting lines between the points of intersection serve as "optical tracks", along which the automatic image evaluation may proceed systematically from one point of intersection to the next. In this way, they establish the neighborhood relations between the markers that contribute to encoding or the non-encoded markers both in the vertical and horizontal directions.

Figure 1:
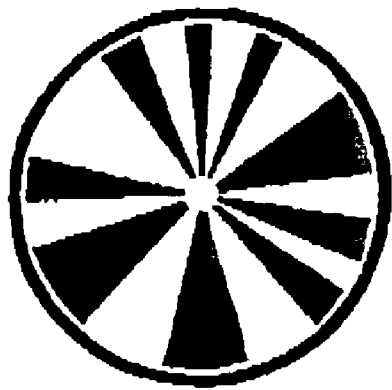
FIG. 1 shows two different encoded point markers according to the prior art.
Figure 1:

In order to allow a 3D reconstruction of the markers provided and secured on the knee envelope based on two overlapping image recordings using the methods of photogrammetry, the pixel coordinates of the homologous point markers need to be determined, something which is also referred to as registration. In an automatic registration, those markers which correspond to each other need to be found from two overlapping image recordings using methods of 2-dimensional image processing. In the prior art his is achieved by the use of individually encoded, relatively large-surface point markers as are illustrated in FIG. 1, for example. Then, with the aid of automatic image processing according to the prior art, point markers are found in two images, their code is read, and then a list of the corresponding markers, i.e. the homologous point markers, is prepared. When the preparation of this list is complete, a 3D data record containing the XYZ space coordinates of all homologous point markers may be established using the known methods of image orientation and bundle adjustment.

In accordance with the invention, on the other hand, a characteristic sequence of simple and very small point markers of different types is used to characterize connecting markers (e.g., lines that connect the point markers with each other) on each of which a specific subset of the point markers and especially the point markers that do not contribute to encoding is arranged in succession. The unique association of the point markers that do not contribute to encoding may be obtained here from the neighborhood relations between the encoded markers.

In addition, in accordance with the invention a space-saving encoding is used which is structured in such a way that the individual code positions of the encoded marker may each be used as a photogrammetric point marker. In so doing, a four-digit code, for instance, is formed not only by one point marker, but from four point markers. In the usual method involving point markers encoded with radial segments (see left-hand side in FIG. 1) there is only one single point marker per code (i.e. for all of the code elements together). The method according to the invention therefore multiplies the number of available point markers by the factor N, where N denotes the number of code positions (bit positions in a binary code). Thus, a body part may be digitized considerably more densely because it may be covered with encoded point markers at a higher density.

Figure 5A:
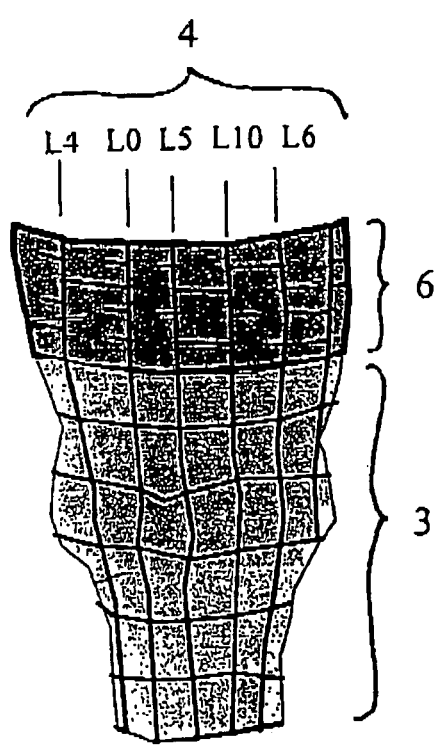
FIG. 5a shows the knee envelope illustrated in FIG. 4, in a first imaging position.
Figure 5B:
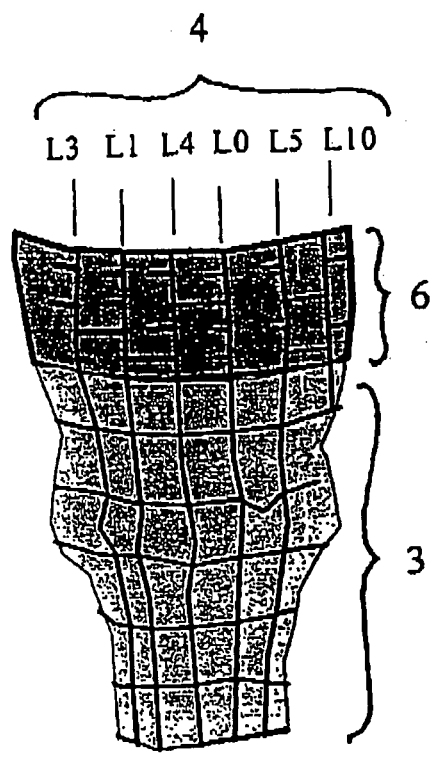
FIG. 5b shows the knee envelope illustrated in FIG. 4, in a second imaging position.

FIGS. 5a and 5b show two images of the knee provided with the envelope, taken from the different imaging positions, A5 and A4 (see FIG. 3 in this respect). On the knee to be digitized, which is a more or less cylindrical body and for which the automatic association of corresponding pixels is to be determined from overlapping peripheral images, the vertical grid lines (the lines oriented along the longitudinal axis of the leg) Li are characterized in the code region 6, identified by the first color, by a binary code having the following two code elements:

horizontal branching from the grid line to the left=logical ZERO=O horizontal branching from the grid line to the right=logical ONE=L.

The image A5 in FIG. 5a shows a four-digit binary code that uniquely encodes each vertical line (connecting marker 4):

Line L 4=(OLOO)
Line L 0=(OOOO)
Line L 5=(OLOL)
Line L 10=(LOLO)
Line L 6=(OLLO)

The first code bit is represented, for instance, by the first grid branching tat is encountered starting from the top. Owing to the clearly defined color transition between the code region 6, the surface area of which is dyed with the first color, and the remaining, lower knee region 3, the surface area of which is dyed with the second color, the point of encounter for decoding this code can be automatically found by methods of color and half-tone image processing, even when the camera is rotated or tilted between taking the images or is otherwise brought into an unknown imaging position.

FIG. 5b shows the image A4 taken of the knee covered with the envelope, which was obtained from an imaging direction radially offset through 45 degrees with respect to the image A5.

By an automatic reading of the code of the connecting marker (i.e., the vertical lines 4), the connecting markers mutually corresponding to each other in the two images, A5 and A4, i.e., the homologous vertical lines 4, can be immediately determined.

In the photogrammetric evaluation, now first of all an image processing of the images is performed, in which first the connecting markers 4 mutually corresponding to each other in the images are associated with one another using their respective code, and then the point markers connected with each other by the respective connecting marker are associated with one another with the aid of the connecting marker association in the images, the 3D shape of the object being determined by means of a photogrammetric evaluation method using the point marker association.

In this embodiment of the invention, it is of particular advantage that the "branching" code position may serve at the same time as a photogrammetric point marker. The center of mass of a branching to the left or to the right may be determined in the image evaluation just as precisely as the center of mass of a continuous grid cross. Thus, in contrast to the known methods, this encoding is extremely space-saving.

A particular advantage of the invention consists in that each code position represents a point marker. Thus, such a code occupies little of the space required for the digitization because it is spread over a plurality of compact point markers.

Figure 6:
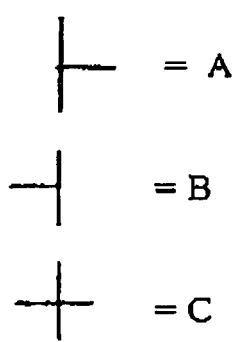
FIG. 6 shows the form of photogrammetric marking used in a further embodiment of the invention.
Figure 6:
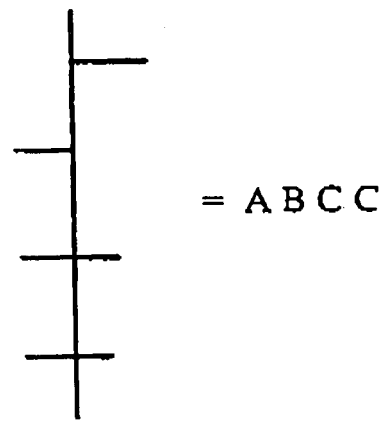

Of course, this code need not be restricted to a binary code. FIG. 6, for instance, shows an encoding of the connecting markers (vertical lines) using a ternary code which consists of the following elements, horizontal branching to the left=A
horizontal branching to the right=B
branching to the left and to the right=C With the aid of merely 3 different types of junctions (=code positions) it is already possible to uniquely encode 3*3=9 connecting markers (lines) so that such a code again takes up considerably less space than the binary code.

Under some circumstances it may be advantageous to have more codes available than are required for the unique identification of all connecting markers, since additional codes may be used for code protection, error recognition and error correction. The use and interpretation of redundant codes occurring herein for an automatic error correction and error recognition of errors occurring in code reading are known to those of ordinary skill in the art of encoding.

It is apparent that the principle in accordance with the invention may be employed in a multitude of different point markers, the point markers not necessarily needing to consist of crosses or lines that encounter each other. All that is required is the provision of at least two different types of point markers, the exact shape of the point markers being irrelevant; conforming to their function as point markers, they only need to be suitable to specify the location of a point on the object.

Figure 7:
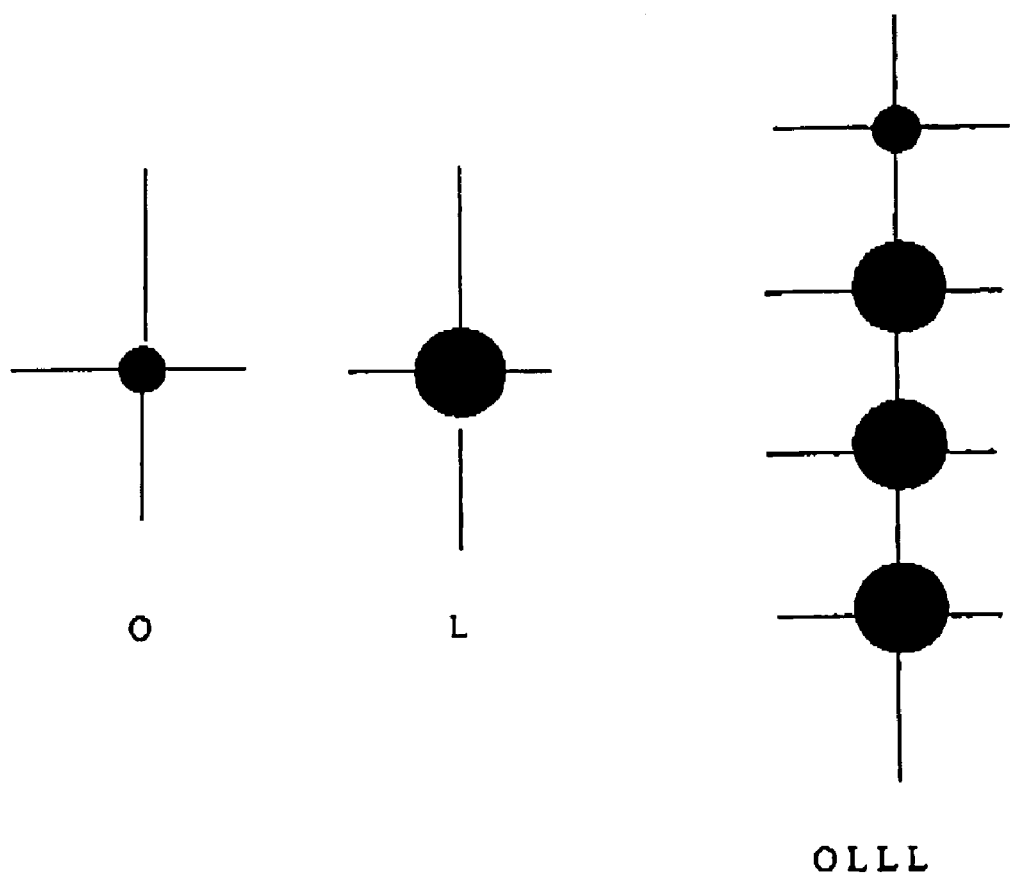
FIG. 7 shows the form of photogrammetric marking used in a further embodiment of the invention.

Accordingly, with reference to FIG. 7, an embodiment of the invention is illustrated in which black points having different diameters are employed as point markers, with a point having a small diameter (on the left in FIG. 7) marking a logical zero and a point with a large diameter (in the center of FIG. 7) marking a logical one of the code.

In this way, the code "O L L L" is produced, for example, by placing one small and three large black circles one behind the other, see on the right in FIG. 7.

It is, of course, not absolutely required to use vertical straight lines as connecting markers connecting the point markers with one another. For instance, horizontal lines or curved lines may be used just as well. What is important is that the connecting markers produce a connection between the point markers that are to be associated with the connecting markers. It is therefore further conceivable for the connecting markers themselves to consist of points.

Thus, in accordance with the invention, three objects are achieved by this marking according to the invention: a large-surface area encoding of a structure (heavy grid lines in the example described) is made possible where the encoding is able to be acquired even by a poor resolution camera; such encoding may be utilized at the same time as a multitude of precisely positioned photogrammetric point markers; and an automatic determination of homologous point markers may be carried out with the aid of the determination of homologous connecting markers.

In other embodiments of the invention, the areas provided for distinguishing between point markers that contribute to encoding and point markers that do not contribute to encoding may, of course, be made to contrast with each other by the most varied of optical configurations. Such optical configuration need not necessarily consist in a different color, but may also consist in a characteristic half tone, a characteristic texture, i.e. a characteristic pattern or a characteristic structure, a characteristic gloss, a surface coating applied to the surface and having a characteristic degree of polarization, characteristic fluorescence properties, certain spectral signatures, a specific local gloss, a specific local temperature, or a characteristic combination of the above-listed optical configuration features.

The high-contrast structures applied for the purpose of photogrammetric marking may further distinguish themselves by reflection characteristics in regard to a spectral range outside the visible range. For instance, they may contrast with the background only in the near infrared range, in the ultraviolet range or in some other range of wavelengths not visible to the human eye. In this way, elastic envelopes may be produced having, e.g. an visible marking or a marking covered by a visible coloration intended for the human eye. They may be in the form of swimsuits, for example, which on the one hand may be designed with an "aesthetic" pattern that is visible to the human eye and, in addition, configured with an invisible surface marking adapted to be detected by photogrammetry and consisting of point and connecting markers.

The invention claimed is:

1. A method of detecting the 3D shape of an object by photogrammetry, comprising the steps of:
   providing a plurality of photogrammetric point markers and a plurality of connecting markers on the surface of the object, each connecting marker connecting a subset of the plurality of point markers with each other, with at least two different types of point markers existing that differ from each other in their optical configuration;
   some of the point markers provided along a connecting marker being formed in such a way that the sequence of their optical configurations results in a predetermined code that characterizes the respective connecting marker;
   taking a plurality of photogrammetric images of the object from different views;
   performing an image processing of the images, in which first the connecting markers mutually corresponding to each other in the images are associated with one another using their respective code, and then the point markers connected with each other by the respective connecting marker are associated with one another with the aid of the connecting marker association in the images; and
   using the point marker association, determining the 3D shape of the object by means of a photogrammetric evaluation process.

2. The method as claimed in claim 1, wherein the connecting markers consist of lines.

3. The method as claimed in claim 2, wherein the lines are straight.

4. The method as claimed in claim 2, wherein the lines are curved.

5. The method as claimed in any of the preceding claims 2 to 4, wherein the point markers are each defined by two lines meeting each other, one of which is part of a connecting marker that connect a subset of the point markers with one another.

6. The method as claimed in claim 5, wherein the different optical configuration of the point markers consists in that some point markers run from the one side of the line forming a connecting marker toward such line to end thereat, and some other point markers run from the other side of the line forming a connecting marker toward such line to end thereat, the sequence of point markers running toward the line from the one side or from the other side resulting in the code characterizing the connecting marker.

7. The method as claimed in claim 5, wherein the different optical configuration of the point markers consists in that some point markers run from one side toward a line forming a connecting marker to end at the line, and some point markers cross the line forming a connecting marker, the sequence of point markers running toward the line from one side and crossing point markers resulting in the code characterizing the connecting marker.

8. The method as claimed in any of claims 1 to 4, wherein the point markers are formed by circles.

9. The method as claimed in claim 8, wherein the different optical configuration of the point markers consists in that the points have different diameters.

10. The method as claimed in claim 1, wherein the point markers that form a code are backed by an area having a first type of optical configuration, and the remaining point markers that do not form a code are backed by an area having a second type of configuration that differs from the first type.

11. The method as claimed in claim 10, wherein the different optical configuration of the areas consists in that the areas have different colors.

12. The method as claimed in claim 1, wherein the point and connecting markers are provided on the object by pulling an elastic envelope having the markers applied thereto over the object.

13. The method as claimed claim 1, wherein the point and connecting markers are provided on the object by applying the markers onto the object using paint.

14. The method as claimed in claim 1, wherein the point and connecting markers are provided on the object by projecting the markers onto the object.

15. The method as claimed in claim 1, wherein the point and connecting markers are provided on the object by sticking self-adhesive films having the markers applied thereto onto the surface of the object.

16. The method as claimed in claim 1, wherein the object is a body part of a human being.

17. A system for detecting the 3D shape of an object by photogrammetry, comprising an imaging system for obtaining photogrammetric images of different views of the object and a system for processing and evaluating the images and for determining the 3D shape of the object, wherein the system for detecting the 3D shape of an object by photogrammetry further includes a plurality of photogrammetric point markers and a plurality of connecting markers on the surface of the object, each connecting marker connecting a subset of the plurality of point markers with each other, with at least two different types of point markers existing that differ from each other in their optical configuration, and some of the point markers provided along a connecting marker being formed in such a way that the sequence of their optical configurations results in a predetermined code that characterizes the respective connecting marker.

18. The system for detecting as claimed in claim 17, further including an elastic envelope which has the point and connecting markers applied thereto and is designed such that it can be pulled over the object and adapts to the shape of the object.

19. The system for detecting as claimed in claim 17, further including one or more self-adhesive films having the point and connecting markers applied thereto and designed such that when stuck on the surface of the object, they are in tight-fitting contact with the object.

20. The system for detecting as claimed in claim 17, further comprising a projection system designed to be used for projecting the point and connecting markers onto die object.

21. The system for detecting as claimed in claim 17, wherein the object is a body part of a human being.

* * * * *